United States Patent [19]

Wagner

[11] 4,309,614
[45] Jan. 5, 1982

[54] DEVICE FOR COMPUTED TOMOGRAPHY

[75] Inventor: Wolfgang Wagner, Hamburg, Fed. Rep. of Germany

[73] Assignee: U.S. Philips Corporation, New York, N.Y.

[21] Appl. No.: 28,776

[22] Filed: Apr. 10, 1979

[30] Foreign Application Priority Data

Apr. 10, 1978 [DE] Fed. Rep. of Germany ....... 2815347

[51] Int. Cl.$^3$ ............................................. G03B 41/16
[52] U.S. Cl. ................................. 250/445 T; 364/414
[58] Field of Search ..................... 250/445 T; 364/414

[56] References Cited

U.S. PATENT DOCUMENTS 4,032,784 6/1977 Rich ............................... 250/445 T
4,051,377 9/1977 Kemner ......................... 250/445 T Primary Examiner—Craig E. Church Attorney, Agent, or Firm—Thomas A. Briody; Robert T. Mayer; Jack E. Haken

[57] ABSTRACT

In computed tomography apparatus the radiation intensity of the radiation source remains constant during a measuring operation. This means that in those positions in which the absorption of the radiation through the patient is particularly weak, the patient gets an unnecessarily large dose without any useful effect, as only a distinct number of X-ray quanta is required for a given measuring accuracy. It is an object of the invention to measure the radiation absorption distribution at a reduced dose but without the measuring accuracy being affected. The radiation intensity of the radiation source in a measuring position is made dependent on the mean measuring error of the adjacent measuring position; the mean measuring error does then indeed not remain constant but it fluctuates less than when a constant intensity of the radiation source is used.

5 Claims, 2 Drawing Figures

DEVICE FOR COMPUTED TOMOGRAPHY

The invention relates to a device for determining the radiation absorption distribution in a plane of examination, comprising at least a radiation source for irradiating the plane of examination from a large number of directions, at least one detector device for measuring the intensity values of the radiation passing through the plane of examination, a measuring device for measuring the intensity of the primary radiation before it is passed through the plane of examination, a first arithmetic device for determining the absorption distribution in the plane of examination from the intensity values and an adjusting element for influencing the primary intensity. The adjusting element is controlled so that the primary intensity is larger at a strong absorption and smaller at a weak absorption.

Such a device is disclosed in the German Offenlegungsschrift 25.43.136 and German Offenlegungsschrift 25.55.675. Therein, a control circuit is provided which controls the intensity of the radiation source so that the intensity of the radiation, after having been passed through the plane of examination is constant. The absorption (more precisely, the line integral of the absorption on the radiation path from the radiation source to the detector device) is computed from the logarithm of the quotient of the radiation intensity before and after passage through the plane of examination. The intensity of the radiation before passing through the plane of examination, that is to say the primary intensity, can be measured by means of a detector which responds to the radiation, but it is alternatively possible to measure a quantity which is characteristic of the radiation intensity, such as, for example, the intensity of the X-ray tube current, provided the voltage of the X-ray tube is not changed by the control, or to measure the control quantity which influences the element.

Relative to the devices wherein the primary intensity is kept constant and the intensity of the radiation passing through the plane of examination varies in dependence on the absorption of the object in the plane of examination, the devices described above have the advantage that, while the dose for the patients remains the same the accuracy increases or that, for the same accuracy, the dose for the patient is reduced. The accuracy is determined by the signal-to-noise ratio of the detector output signals supplied by the detector device. This signal-to-noise ratio becomes more favourable according as the intensity of the radiation after having passed the plane of examination is larger.

For the devices wherein the primary intensity is constant this means that this primary intensity must be chosen so high that also during the examination of strongly absorbing areas a sufficient signal-to-noise ratio is obtained. This indeed results in a still larger signal-to-noise ratio for the less strongly absorbing portions of a body, but this hardly contributes to an improvement of the overall accuracy. The absorption of a portion in the examined body is namely computed from the measuring values which are measured along radiation paths which only pass through that portion and which, depending on the direction of the radiation path, have a strong or a weak absorption, that is to say a larger or a smaller signal-to-noise ratio. However, the error in the reconstruction of the absorption distribution in the portion predominantly depends on the small signal-to-noise ratio of the measuring value which is associated with a radiation path having a strong absorption.

Compared therewith, the primary intensity of the radiation is reduced at the less strongly absorbing portions of the patient in a device of the type mentioned in the preamble. This results in a reduced radiation load of the patient, without reducing the accuracy, because the signal-to-noise ratio is kept equal at all values. Such a control loop for keeping the intensity of the radiation constant before it is passed through the plane of examination is only suitable for computed Tomography (CT) devices of the so-called first generation, that is to say for CT devices the detector device of which comprises only one detector element, which measures the absorption along a narrow beam path in the plane of examination. In these devices the radiation source-detector system is laterally displaced during the examination, so that the measuring beam consecutively measures the plane of examination along a plurality of parallel measuring paths. Thereafter, the radiation source-detector system is rotated over a small angle, whereafter the radiation source-detector system is laterally displaced etc.

For the considerably faster CT apparatus of the second and the third generation, respectively, wherein the absorption is measured simultaneously along a large number of measuring paths which divide the body in a fan-shaped manner, such a control circuit cannot be used without further measures, as the intensity of the radiation after it has passed the plane of examination cannot be kept constant simultaneously in all the areas defined by the measuring paths.

In addition, it should be borne in mind that only a single value is required for the control of the primary intensity. The period of time for the measurement of a measuring value must exceed the control period in the control circuit, as a result of which either the period of time for the determination of all measuring values (the CT apparatus, used in paractice, require 30,000 measuring values and even more for the reconstruction of the absorption distribution in the plane of examination) becomes very long or a very rapid and expensive control circuit must be provided.

It is an object of the invention to provide in the different types of computed tomography apparatus wherein some or a large number of absorption values must be measured, with the aid of simple means, either an improvement in the accuracy of the measurements without increasing the radiation load of the patient and the thermal load of the X-ray tube or a decrease in the radiation load of the patient and the thermal load of the tube, without detracting from the accuracy.

A device according to the invention is characterized in that a further arithmetic device is provided for determining, from measuring values along all measuring parts an adjusting quantity from each angular position for controlling the adjusting elements, which further arithmetic device comprises a first arithmetic unit for determining from all measuring values of the intensity $(I(\theta,p))$ at an angular position $(\theta)$, a mean noise value $(S(\theta))$ which is proportional to the sum of the quantum noise of all measuring values, a second arithmetic unit for determining a ratio from the mean noise value determined by the first arithmetic device and a constant predetermined maximum noise value, a third arithmetic unit for determining from this ratio an adjusting quantity which is a square root of the ratio, an output of this third arithmetic unit being connected to an input of the adjusting element.

For first generation computed tomography apparatus, that is to say for apparatus of the type mentioned in the opening paragraph which have only one detector element, the angular position of the radiation source and detector device is determined by the angle which encloses the measuring path between the radiation source and the detector element with a preselected straight line in the plane of examination. For third generation computed tomography apparatus, wherein the detector device comprises a row consisting of a large number of separate detector elements, the angular position of the radiation source and detector device is the angle between a central measuring path, that is to say the measuring path which coincides with a connecting line between the radiation source and the point of rotation of the radiation source-detector device system, and a preselected reference line. So, in this case, the mean noise value is formed from those measuring values which are measured in one of the many positions of the radiation source-detector device system along measuring paths extending in a fan-shaped manner from the radiation source and are below an intensity limit value, that is to say which are attenuated to a certain extent by the body in the plane of examination.

To ensure that in no angular position of the radiation source-detector device system the means adjusting quantity results in a value at which the primary intensity would become greater than the maximum permissible primary intensity, the mean noise value must be adjusted in proportion to the maximum mean noise value relative to all angular positions, so that a ratio is obtained. The noise values of a preliminary measured adjacent plane of examination of the examined body can be used for the determination of this maximum mean noise value, as in that case it may be assumed that in this adjacent plane of examination the ratios are similar to those in the plane still to be examined. If such noise values are not yet available, a so-called coarse measurement with a considerably reduced (for example with a reduction factor 1:100) primary intensity can be performed, it then being necessary to multiply afterwards the noise values thus obtained by the inverted value of the reduction factor. Alternatively, the maximum mean noise value can also be estimated on the basis of the dimensions of the patient in the plane to be examined. The dimensions of the patient or the contour of this cross-section in the plane of examination can possibly be measured by means of an optical scanning device, coupled to the examination apparatus, it being possible to obtain an approximation of the maximum mean noise value by assuming that the body in the plane to be examined has a substantially uniform absorption distribution.

The primary intensity which can be calculated from the square root of the determined ratio or the adjusting quantity of the adjusting element required for this primary intensity is used in one of the following, preferably the next following angular position $\theta$ for the adjusting element. The next following angular position is that angular position which always encloses the smallest angle by means of the considered position and which as a rule is also immediately subsequent thereto in the time. If the time between two immediately consecutive positions is too short for the measurement of the mean noise value and for the corresponding control of the adjusting element, the adjusting element will not be controlled in accordance with the calculated mean noise value until in a second or a further subsequent angular position.

The device repeats these steps after each new angular position of radiation source and detector device. It is of course not possible to determine a mean noise value in advance for the first angular position from the measurement of the absorption in the plane of examination, as this varies considerably from patient to patient. The maximum permissible primary intensity of the X-ray source is, for example, used for this first angular position.

The fluctuations in the radiation intensity of the radiation after it has passed through the plane of examination can be classified into two categories: intensity fluctuations in the different measuring paths at an angular position of radiation source and detector device, which are determined by the different absorption of the radiation along the different measuring paths in the plane of examination, and variations in the mean absorption value from one angular position to the next. The invention is based on the recognition that the firstmentioned fluctuations can indeed not be compensated for, but that this is possible for the second mentioned variations. Considered for all angular positions these variations in the means value can amount to one order of magnitude and more when the body has approximately the shape of an ellipsoid. However, the variations in the mean noise value from one angular position to the next are small, so that, when the mean noise value is known for an angular position, the approximation of the mean noise value for the next angular position can be predicted or placed in the next angular position as a measure of the mean noise value to be expected, respectively, when in the next measurement the body would be irradiated with the same primary intensity. So, the invention does not enable the measurement of each measuring value with the same signal-to-noise ratio, but the measuring values obtained in different angular positions show, on an average, smaller variations in the signal-to-noise ratio than when the primary intensity would remain constant.

An embodiment of the invention will now be described in detail with reference to the accompanying drawing.

Figure 1:
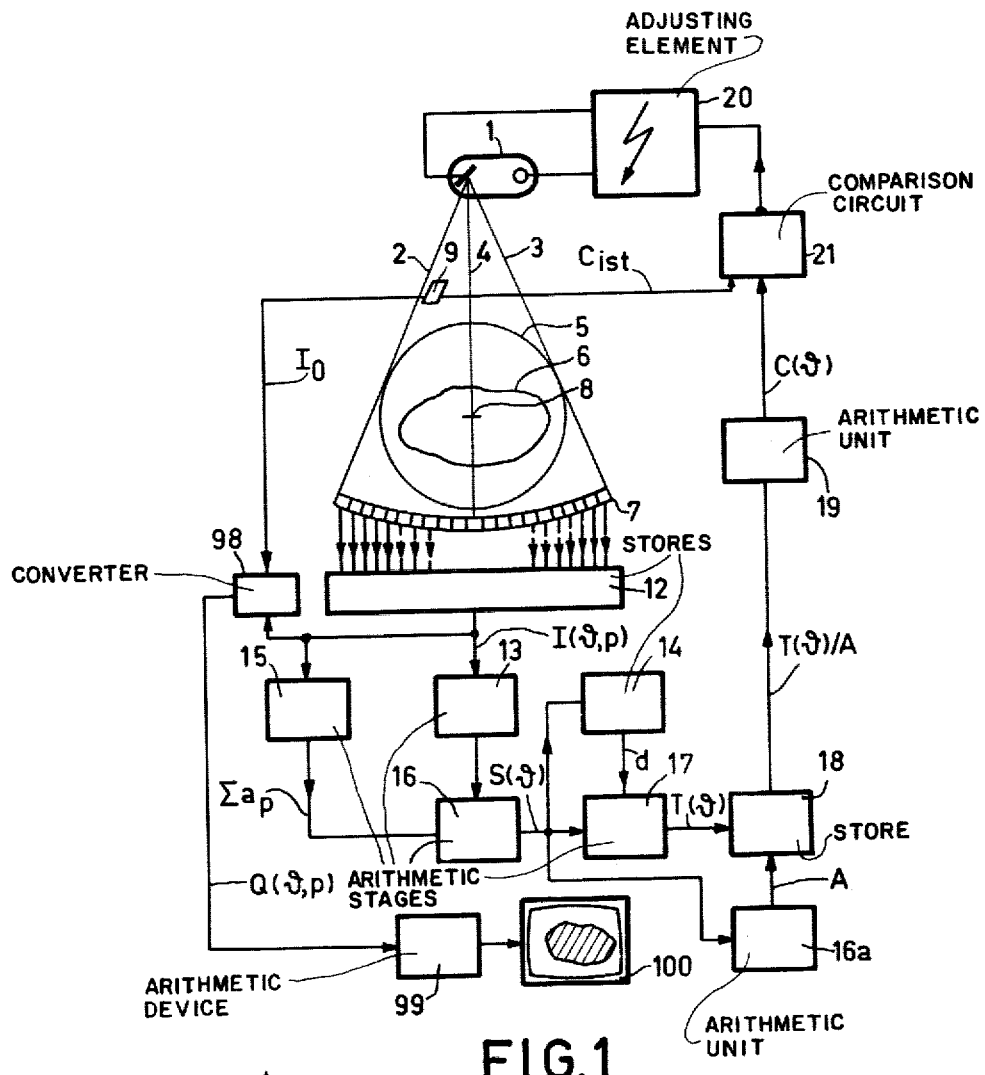
FIG. 1 shows a computed tomography apparatus according to the invention.

In FIG. 1 an X-ray tube 1 which emits a fan-shaped radiation beam containing the marginal rays 2 and 3 and the central ray 4 is used as the radiation source. The body 6 to be examined is positioned in the cylindrical plane of examination 5. The arrangement further comprises a detector device 7 consisting of a large number of detector elements, which are placed closely adjacent to one another in the plane of examination. The radiation source 1 and the detector device 7 are rigidly coupled to one another in a manner not shown in the drawing and are rotatable around an axis 8, which is perpendicular to the plane of examination 5, for passing through a large number of additional angular positions. The plane of examination 5 is defined by the marginal rays 2 and 3. A detector 9 measuring the intensity of the radiation before it passes through the plane of examination 5, that is to say the intensity $I_O$ of the primary radiation, is disposed between the radiation source and the plane of examination 5.

From the measuring values of the intensity of the radiation (also denoted intensity value hereinafter) before (detected by means of the detector 9) and behind (detected by means of detectors 7) the plane of examination the absorption value Q(θ,p) is determined in converter 98 by means of the equation:

$$Q(\theta,p) = \ln I_0(\theta) - \ln I(\theta,p) \qquad (1)$$

In this equation θ is the angular position of radiation source 1 and detector device 7, at which the absorption value was measured, and p the position of a detector element in the detector device 7, with which the associated intensity value I(θ,p) is measured. From the absorption values Q(θ,p), which represent the integral of the absorption along the measuring path connecting the radiation source in the angular position θ to the $p^{th}$ detector, a first arithmetic device 99 computes the absorption distribution which is displayed by means of a display device 100.

Up to this point the device is fully known. As known the measuring error, resulting from quantum noise, is produced in accordance with $$\delta^2(I(\theta,p)) = 1/I(\theta,p)$$

In general, this value is alternatively denoted the variation of the absorption value.

The device comprises an arithmetic device which computes a noise value $$S(\theta): \\ S(\theta) = \left( \sum_p a_p \cdot 1/I(\theta,p) \right) \cdot \frac{1}{\Sigma a_p} \qquad (2)$$

Herein $a_p$ is an evaluation factor which is defined in a practical embodiment by:

$$a_p = 1 \text{ for } I(\theta,p) < I_g \text{ and} \qquad (3) \\ 0 \text{ for } I(\theta,p) \geq I_g,$$

wherein $I_g$ is an upper intensity limit value which is somewhat smaller than the value of the primary intensity $I_0$ for each angular position. The equation (3) means that only those intensity values, which are smaller than $I_0$ and $I_g$, which are therefore hardly attenuated by the body 6, are used for the computation of S(θ). The result is that the measuring values, which are attenuated to a too low extent, are not used for the average noise value formation.

The sum of all evaluation factors $a_p$ represents the number of measuring values I(θ,p) which are smaller than $I_g$. Thus, S(θ) represents the average noise value of the intensity values in the different measuring paths associated with the angular position θ.

To compute S(θ), the measuring values I(θ,p) are transferred from a store 12 to a first arithmetic stage 13, thereafter inverted and finally added together. An arithmetic stage 15 counts the number of intensity values of an angular position θ which are smaller than the intensity limit value $I_g$. The arithmetic stage 15, may, for example, comprise a comparator supplying a signal (for example "1") when I(θ,p) is smaller than $I_g$, and a counter counting these signals.

A third arithmetic stage 16 divides the value $\Sigma_p((I(\theta,p)^{-1}))$, produced by the arithmetic stage 13, by the value $\Sigma a_p$ produced by the arithmetic stage 15, so that the value S(θ) is obtained at the output of the arithmetic stage 16.

Figure 2:
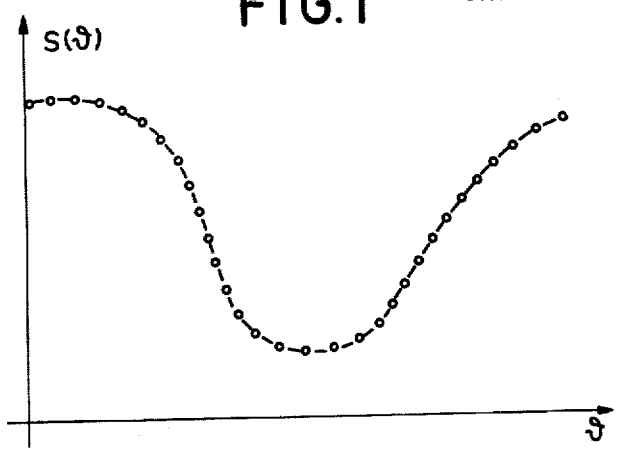
FIG. 2 shows a typical variation of the dependence of the mean measuring error on the angular position.

FIG. 2 shows the arithmetical mean value S(θ) as a function of the angular position θ of radiation source 1 and detector device 7. Their maxima are obtained when the central beam 4 extends approximately into the direction of the main axis of the body 6, which may be considered as being of an ellipsoidical shape, that is to say into the direction transverse of the position shown in the drawing; the minimum is obtained in the direction perpendicularly thereto (the position shown in the drawing). The drawing shows that S(θ) varies regularly, the values S(θ) associated with adjacent angular positions differing only little from each other. It is therefore possible to predict the value S(θ) of a certain angular position in accordance with the known mathematical extrapolation methods, if the values $S(\theta_i)$ for the preceding (adjacent) angular position is known. Thus it is possible to compute a prediction value T(θ) from the average value S(θ), using the following equation:

$$T(\theta) = d_1 \cdot S(\theta_{-1}) + d_2 \cdot S(\theta_{-2}) + d_3 \cdot S(\theta_{-3}) + \qquad (4)$$

where $\Sigma_i d_i = 1$

Therein $\theta_{-1}$ is the adjacent angular position preceding the angular position θ, $\theta_{-2}$ the angular position occupied before $\theta_{-1}$ etc. In the most simple embodiment $d_1 = 1$ and $d_2 = d_3 = \ldots = d_i = 0$. If the time required to perform the above-mentioned computations exceeds the time period between two measurements in adjacent angular positions, the following values may, alternatively, be used, for example $d_1 = d_3 = d_4 \ldots = d_i = 0$ and $d_2 = 1$. So in these methods the prediction value T(θ) corresponds to the average measuring value measured in one of the preceding angular positions. The coefficients $d_1$ to $d_i$, inclusive (where i is, for example, equal to 3) can, however, also be determined by means of other known prediction methods, wherein, for example, also the ascending and descending portions of the curve are taken into consideration.

The value T(θ) is formed from the value S(θ) in the arithmetic stage 17 by means of the equation (4), the value $S(\theta)_m$ supplies the associated coefficients $d_i$ via a store 14 in which the pre-calculated value S(θ) and the coefficients $d_i$ were stored. The calculated value T(θ) is stored in an intermediate store 18. A value C(θ) is computed in the arithmetic unit 19 from the value T(θ) in accordance with the equation:

$$C(\theta) = (T(\theta)/A)^\lambda$$

where $0 < \lambda < 1$

Therein, A is a constant factor determined prior to the measurement of the intensity values of a plane of a body and C(θ) the factor by which the primary intensity in the next angular position must be changed.

The factor A corresponds to the maximum average measuring value $S_m(\theta)$ relative to all angular positions and is obtained in the manner described above from the previously measured measuring values, because the arithmetic stage 16a stores all values S(θ) of a previously performed measurement (for example of an adjacent plane of examination) and calculates the maximum mean measuring values $S_m(\theta)$ by a simple adding and dividing operation. The value $S_m(\theta)$ is the required value A. From investigation it become apparent that optimum results are obtained at a value $\lambda = 0.5$ (which corresponds to a square root) or a value which deviates only slightly therefrom. The primary intensity is constant at $\lambda = 0$ (as in the prior art X-ray diagnosis apparatus) and considerably poorer ratios are obtained, which also occur at the value $\lambda = 1$.

The value $C(\theta)$ is used to control a supply source comprising adjusting element 20, which changes the maximum permissible primary intensity $I_O$ of the radiation emitted by the radiation source 1 by a factor of $C(\theta)$. For this purpose a control circuit is preferably provided which comprises a comparison ciruit 21 to one input of which the value $C(\theta)$ is applied as the setting value and the measuring signal $C_{ist}$ to a further input of the detector 9, with which the primary intensity $I_O$ is measured. The difference between the values $C(\theta)$ and $C_{ist}$ controls the adjusting element 20 so that with the measured primary intensity $I_O$ the calculated predetermined mean intensity behind the plane of examination is, at least approximately, obtained.

Alternatively, the arithmetic stages 13, 16, 16a and 17, possibly also the arithmetic unit 19 may, if so desired, be replaced by one single suitably programmed digital computer. However, the output signals of the detector device 7 can also be processed in an analog manner.

The invention can, alternatively, be used with computer tomography apparatus which have a large number of radiation sources which are equidistantly distributed along the circumference of a circle, each having an associated detector device, which can be sequentially actuated. A primary radiation intensity which is calculated from the mean absorption value, which was measured by the detector device associated with the adjacent radiation source is then produced by a radiation source.

What is claimed is

1. In a device for determining the radiation absorption distribution in a plane of examination which comprises radiation source means for irradiating the plane of examination with penetrating radiation from a large number of directions; detector means including a plurality of detector elements for measuring intensity values of the radiation which passes through the plane of examination; measuring means for measuring the intensity of the radiation before it passes through the plane of examination; first arithmetic means for determining the absorption distribution in the plane of examination from the intensity values; and adjusting means for influencing the intensity of radiation emitted by the source means so that said intensity is larger in first regions of the plane then it is in second regions of the plane, said first regions absorbing radiation more strongly then said second regions;

wherein, as an improvement, the device further comprises additional arithmetic means for producing, for measuring values along all measuring paths at each angular position, adjusting signals for controlling the adjusting means, which additional arithmetic means include:

second arithmetic means for determining a mean noise value ($S(\theta)$) over all measuring values of the intensity ($I(\theta)$, p)) obtained from a detector element at position p within the detector means and at an angular position ($\theta$), which is proportional to the sum of the quantum noise of all measuring values;

third arithmetic means for determining a ratio of the mean noise value determined by the second arithmetic means and a predetermined, constant, maximum noise value; and fourth arithmetic means for producing the adjusting signal from the ratio, the adjusting signal being the $\lambda$ power of the ratio, $\lambda$ being greater than zero and less than one, the adjusting signal being applied to control the adjusting means.

2. A device as claimed in claim 1 wherein the adjusting means include a differential amplifier having two inputs, the output of the adjusting means being controlled by the output of the differential amplifier, the adjusting signal being applied to one input of the differential amplifier and an output of the measuring means which is proportional to the intensity of radiation before it passes through the plane of examination being connected to the other input of the differential amplifier.

3. A device as claimed in claim 1 or claim 2 wherein the fourth arithmetic means is a non-linear amplifier.

4. A device as claimed in claim 1 or claim 2 wherein $\lambda$ equals one half.

5. A device as claimed in claim 3 wherein $\lambda$ equals one half.

* * * * *